United States Patent [19]

Wakai et al.

[11] 4,442,493

[45] Apr. 10, 1984

[54] CUTTING TOOL RETREAT AND RETURN FOR WORKPIECE PROTECTION UPON ABNORMALITY OCCURRENCE IN A PREPROGRAMMED MACHINE TOOL

[75] Inventors: Hideyuki Wakai; Masataka Kashimoto; Chiaki Sakamoto; Eiji Mizutani, all of Hirakata, Japan

[73] Assignee: Kabushiki Kaisha Komatsu Seisakusho, Tokyo, Japan

[21] Appl. No.: 279,033

[22] Filed: Jun. 30, 1981

[30] Foreign Application Priority Data

Jul. 4, 1980 [JP] Japan .................................. 55-91368
Jul. 4, 1980 [JP] Japan .................................. 55-91369

[51] Int. Cl.³ ........................ G06F 15/46; G05B 19/18
[52] U.S. Cl. ........................................ 364/475; 408/6;
408/11; 408/13; 364/474; 83/62.1; 82/2 B
[58] Field of Search ............... 364/506, 507, 474, 475;
408/1, 3, 5-7, 11, 13; 82/1 C, 2 B; 83/62.1, 61,
62, 71, 72

[56] References Cited

U.S. PATENT DOCUMENTS

| | | | |
|---|---|---|---|
| 3,675,517 | 7/1972 | Tadayoshi | 408/11 |
| 3,690,202 | 9/1972 | Tebo | 408/5.2 |
| 3,723,017 | 3/1973 | Bilz et al. | 408/6 |
| 3,859,001 | 1/1975 | Hoddinott et al. | 408/3 |
| 4,045,660 | 8/1977 | Weisgerber et al. | 235/151.11 |
| 4,266,120 | 5/1981 | Johnstone | 235/92 CT |
| 4,288,849 | 8/1981 | Yoshida et al. | 364/102 |
| 4,325,015 | 4/1982 | Heiberger | 82/2 B |
| 4,338,556 | 7/1982 | Hetzel | 318/569 |
| 4,355,466 | 10/1982 | Shimajiri | 29/26 A |
| 4,390,953 | 6/1983 | Johnstone | 364/474 |

Primary Examiner—James D. Thomas
Assistant Examiner—Archie E. Williams, Jr.
Attorney, Agent, or Firm—Spensley, Horn, Jubas & Lubitz

[57] ABSTRACT

A numerically controlled (NC) machine tool has apparatus for automatically positioning and feeding a cutting tool to follow a programmably predetermined path. Sensing devices are provided to detect when the cutting tool suffers an abnormality, such as becoming dull or chipped. The feed devices of the NC machine tool are then commanded, by an arithmetic unit having a memory and by an NC command generating unit, to automatically retreat the cutting tool. It retreats, without interference with the workpiece, to a first position, parametrically determined by the shape and size of the workpiece, cutting tool data for the abnormality, completion and tool exchange positions, and by the nature of the machining operation. This retreat location is a position at which the cutting tool may be replaced. After replacement of the cutting tool, the cutting tool is automatically returned, via the first position, to a second position from which the machining is resumed. The second position is determined by the arithmetic means to provide for repeated machining of a portion of the surface of the workpiece leading to the position at which the abnormality was sensed.

11 Claims, 16 Drawing Figures

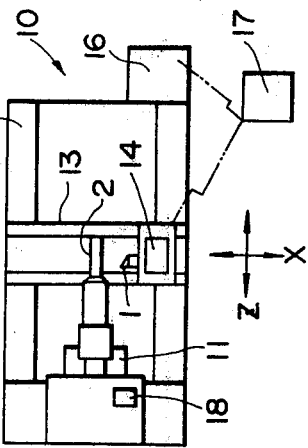
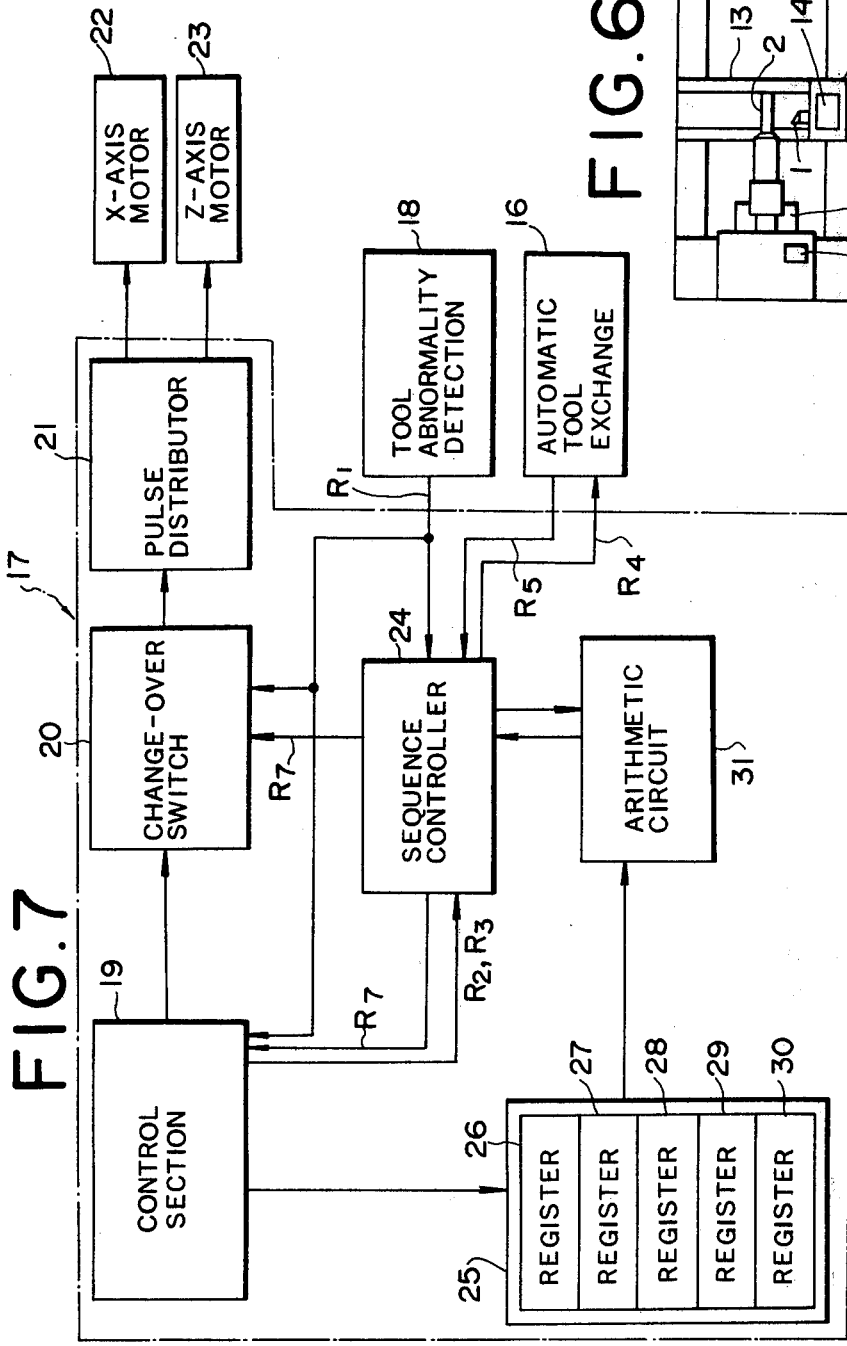

CUTTING TOOL RETREAT AND RETURN FOR WORKPIECE PROTECTION UPON ABNORMALITY OCCURRENCE IN A PREPROGRAMMED MACHINE TOOL

BACKGROUND OF THE INVENTION

This invention relates, in a numerically controlled (NC) machine tool, to a method for detecting the occurrence of an abnormality in the cutting tool and for deciding an appropriate retreat path for the cutting tool to a tool replacement position and a compatible return path to the workpiece.

In the prior art, when an abnormality occurs in the cutting tool of NC machine tool during its automatic machining operations, an exchange of the cutting tool is conducted at a predetermined place to which the cutting tool is manually transferred after the operation of the NC machine tool has been stopped. To resume the machining operations on a workpiece, both the cutting tool and the controlling program for the NC machine tool must be manually brought back to the positions corresponding to the top of a block of cutting tool path data, during which block the NC machine tool has been stopped. In some instances, only a full restart is possible. Such manual operations require that a great deal of time and effort be devoted to the tool exchange. Additionally, there is a high probability that the cutting tool with inadvertently come into contact with the workpiece during the retreat and return movements, causing further damage to the workpiece, which may require discarding the damaged work.

Such inadvertent damage to the workpiece may be avoided by choosing the retreat and return paths in accordance with the situation existing when the abnormality arises. One potential solution established by the prior art is to memorize all paths taken by the cutting tool before the abnormality is sensed and a retreat command signal is generated and the path is retraced in reverse. However, such systems become complicated and cumbersome, and may cause scratching of the surface of the workpiece during the reverse operation. Further, it is then difficult to restart the machining except from the beginning.

In another example, a system is so constructed and governed so as to automatically retreat and then return the cutting tool over a predetermined retreat and return path when commanded by an abnormality signal. However, in such a system, the retreat and return paths of the cutting tool are conducted in the same manner regardless of the machining operation being performed and without consideration of the size and shape of the workpiece. Operations, such as external diameter machining, edge face machining, and internal diameter machining, each require unique retreat and return paths to be followed by the cutting tool in order to avoid contact between the cutting tool and the workpiece. The prior art does not appear to take such machining mode differences into consideration.

Several methods for detecting an abnormality in the cutting tool are shown in the prior art. One such method is to detect the electric current of the main spindle motor of the NC machine tool and to judge, by an increase in that motor current, that an abnormality has occurred in the cutting tool. A second method is disclosed in which the vibration of a portion of the NC machine tool is picked up by appropriate sensors and the judgment is made on the basis of the amplitude of the vibration. Neither the the main spindle motor current nor the vibration amplitude of the machine tool consistently represent an indication of cutting tool abnormality. Still another method has been proposed in which the force applied to the cutting tool during the machining operation is used for abnormality judgment. However, in this method, a sensor must be provided in close proximity to each cutting tool in order to sense the force applied to the cutting edge of the cutting tool. By being exposed to the environment in the vicinity of the cutting operation, the durability of the sensor and the inherent problems of the lead wire connections between the sensor and that portion of the NC machine tool utilizing the sensor output gives rise to reduced reliability.

SUMMARY OF THE INVENTION

In the present invention, means are provided to sense the occurrence of an abnormality in the cutting tool of an NC machine tool. The output of the sensing means is monitored by control means associated with the NC machine tool. During the machining of a workpiece, the control means of the NC machine tool command the position and feed functions determining the path to be followed by the cutting tool of the NC machine tool. When the control means determines that an abnormality has occurred in the cutting tool, by a change in the output from the sensing means, the programmed machining operation is interrupted, and the present cutting tool position is retained. Based upon information found in the program controlling the normal machining operations, the mode of machining operation is determined to be either external diameter machining, edge face machining, or internal diameter machining. This information, combined with the position at which the abnormality occurred and the machining mode, and with a programmed parameter relating to the size of the workpiece, are mathematically processed by this invention to determine a retreat path to a first position of clearance from the workpiece and thence, avoiding contact with the workpiece, to a position at which the cutting tool may be exchanged. Appropriate drive command signals are provided to the NC machine tool to move the cutting tool along this computed retreat path.

Upon completion of the tool exchange, additional command signals are provided to return the cutting tool to the workpiece via the previously identified first retreat position, but rather than proceeding directly to the position at which the abnormality occurred, the cutting tool is returned to the normally programmed machining path at a point preceding, in sequence, said abnormality position in order to provide an overlapping of machining in that region. When the cutting tool again reaches the position at which the abnormality had occurred, control of the position and feed of the cutting tool reverts to the program of the NC machine tool until such time as a further abnormality indication is received.

Accordingly, it is an object of this invention to provide, in a numerically controlled machine tool, a method and device for automatically determining cutting tool retreat and return paths free of interference between the cutting tool and the workpiece being machined, in which selectable modes of cutting tool retreat and return, dependent upon the machining operations being performed, are chosen by information partially computed from special input data and partially within the control program of the NC machine tool.

Another object of this invention is to provide a method and device for automatically determining cutting tool retreat and return paths which are free of interference between the cutting tool and a workpiece, in which the machining is resumed at a point which is a predetermined distance closer to the machining start point than the position at which the abnormality occurred so as to remove irregularities on the work made by the abnormal cutting tool.

A further object of this invention is to provide a method and device for automatically detecting abnormality of the cutting tool and therefrom accurately determining cutting tool retreat, cutting tool exchange, cutting tool return, and resumption of machining, and performing such functions and motions in a short period of time.

A still further object of this invention is to provide a method and device for detecting an abnormality in the cutting tool, in which a feed motor current is sensed and the cutting tool abnormality is judged to have occurred when the sensed current exceeds a predetermined value.

BRIEF DESCRIPTION OF THE DRAWINGS

In the accompanying drawings:

FIG. 6 is a schematic representation of a numerically controlled (NC) machine tool employing in this embodiment, FIG. 7 is a block diagram showing an example of a NC unit, illustrating an embodiment of the herein invention.

DETAILED DESCRIPTION OF THE INVENTION

In an embodiment of a method according to this invention, in order to specify the fundamental movement of each tool of an NC machine tool on an tool abnormality occasion, tool retreat and return modes are stored on predetermined blocks of an NC tape. These tool retreat and return modes specify steps to control, for example, motor speed for the feed drives of the NC machine tool. To select these modes, transfer codes, one of the NC information, are also stored on the NC tape. In this embodiment, the transfer codes include those (identified for this discussion as M81, M82, and M83) which respectively correspond to the external diameter machining mode, edge face machining mode and internal diameter machining mode. Each mode includes variables representing retreat start position, retreat position, etc. The retreat start position is decided by reading the tool position at which a tool abnormality signal is received. Data for the retreat position can be stored in a NC tape block which instructs retreat and return operations or a block preceding this block either in advance, or, by an operator, as required. For example, manually operated switch means may be provided for operator entry of this data. Parameters such as relief length l, required in the calculation of tool retreat and return paths to avoid interference between the tool and work, should be stored in advance into a block instructing the retreat and return operations or into a predetermined block preceeding to the above block.

Figure 1:
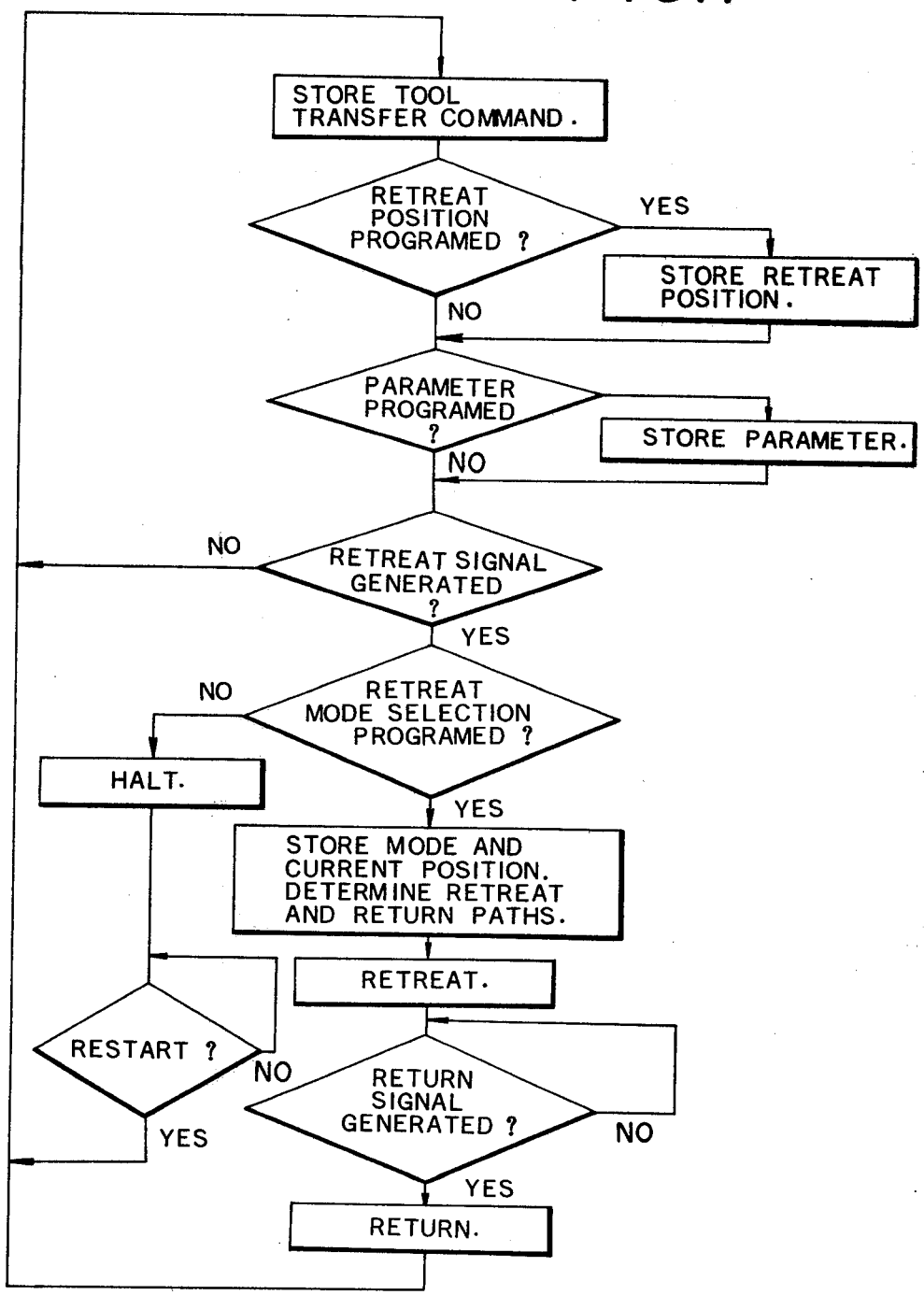
FIG. 1 is a flowchart showing the steps taken by an NC machine tool in an embodiment according to this invention.

Referring now to FIG. 1, the method according to this invention will be described. An NC unit 17 (FIG. 7) stores a tool transfer command value each time a tool transfer command signal is received. When an instruction to store a retreat position A (FIG. 3) and data representing the retreat position A is stored in a block of the NC tape, the NC unit 17 stores the data for the positon A. When a storage instruction and a machining relief parameter l are stored in the NC tape, the NC unit 17 stores the parameter l. Based upon a set of taped or programmed machine instructions, the NC unit 17 controls the normal NC operation until it receives an abnormality signal, generated as described below.

Figure 2:
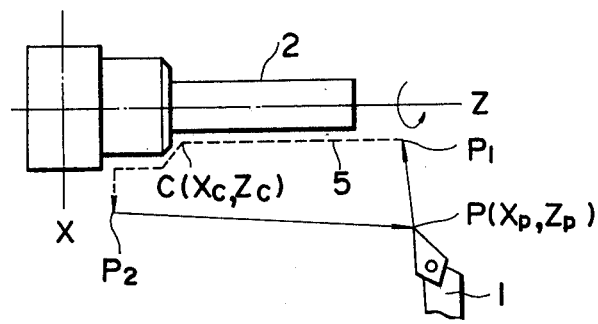
FIG. 2 shows a typical path taken by a cutting tool in an embodiment of this invention, for the performance of an external diameter machining operation.

Referring to FIG. 2, in the normal NC operation, a cutting tool 1 moves from a position P to a position P$_1$, from which the tool 1 starts to be controlled to move along a broken line 5, representing an external diameter machining operation.

When a tool abnormality occurs, for example, at a position C, and an abnormality signal is inputted, the NC unit 17 judges whether or not a transfer code for retreat mode selection (M81, in this case) is stored in a block currently being executed. If M81 is found to be stored in the block, retreat and return paths according to the mode M81 are calculated taking into account the current position, an NC command address, the retreated position, and the parameter l as shown in Table 1. Then the tool 1 is transferred from the current position C to the retreat position A via positions E and F according to transfer steps 1 through 3 in Table 1.

TABLE 1

| Mode | Transfer Step | Retreat Position | Retreat X | Retreat Z | Transfer | Return Position | Return X | Return Z | Transfer |
|---|---|---|---|---|---|---|---|---|---|
| External Mode (M81) | 1 | E | XD + 2a | ZD | Quick | F | XA | ZD | Quick |
| | 2 | F | XA | ZD | " | E | XD + 2a | ZD | " |
| | 3 | A | XA | ZA | " | D | XD | ZD | Machining |
| Edge Mode (M82) | 1 | E | XD | ZD + a | " | F | XD | ZD | Quick |
| | 2 | F | XD | ZA | " | E | XD | ZD + a | " |
| | 3 | A | XA | ZA | " | D | XD | ZD | Machining |
| Internal Mode (M83) | 1 | E | XD − 2a | ZD | " | F | XD − 2a | ZA | Quick |
| | 2 | F | XD − 2a | ZA | " | E | XD − 2a | ZD | " |
| | 3 | A | XA | ZA | " | D | XD | ZD | Machining |

"Quick" in Table 1 means a rapid transfer of a tool without machining operation and "Machining" means transfer of a tool while operating the spindle and feed drives in their normal machining conditions. The X value in Table 1 represents command values expressed relative to diameter and a is a constant.

In the retreat position A, the tool 1 is replaced by a new one and when the NC unit receives a return signal, the tool 1 is transferred from the retreat position A to machining resumption position D via positions F and E in accordance with the return transfer steps 1, 2 and 3 in Table 1. When the tool 1 reaches the machining resumption position D, it resumes machining operation.

Coordinates $(X_D, Z_D)$ of the machining resumption position D are obtained from the following equations (1) and (2).

$$X_D = X_C + \frac{l \cdot (X_C - X_B)}{|X_B - X_C| + 2|Z_B - Z_C|} \quad (1)$$

$$Z_D = Z_C + \frac{2l \cdot (Z_C - Z_B)}{|X_B - X_C| + 2|Z_B - Z_C|} \quad (2)$$

where $X_B$ and $Z_B$ are X and Z values of X- and Z-axes of a machining completion position B; $X_C$ and $Z_C$, X and Z values of X- and Z-axes of the position C; l, a relief programmed according to the machining mode.

Figure 4:
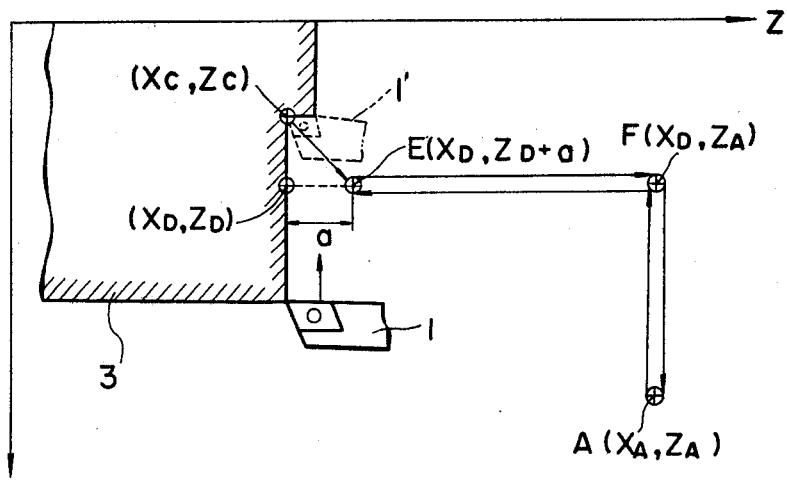
FIG. 4 shows retreat and return paths to be taken by the cutting tool when an abnormality occurs in the cutting tool during an edge face machining operation.
Figure 5:
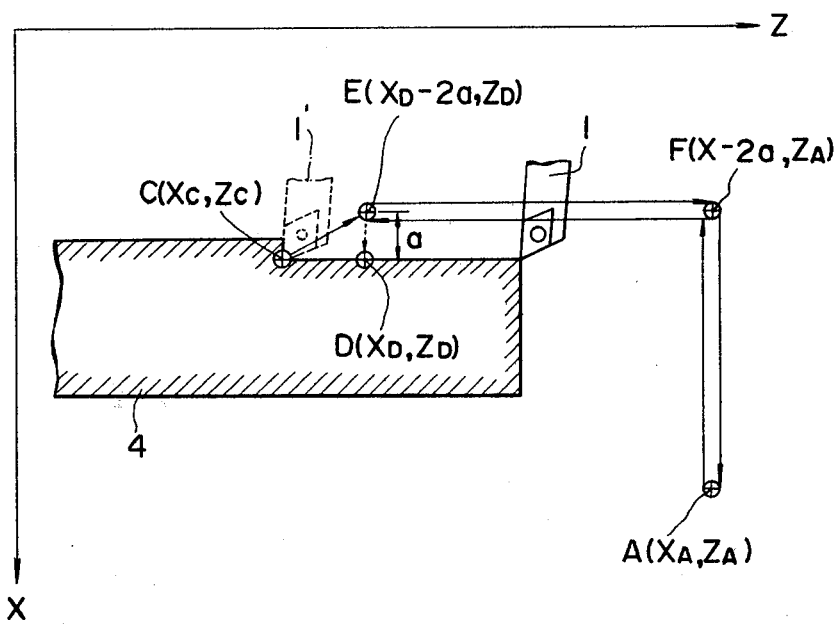
FIG. 5 shows retreat and return paths to be taken by the cutting tool when an abnormality occurs in the cutting tool during an internal diameter machining operation.

Referring to FIG. 4, which shows the retreat and return paths in the edge face mode, the tool 1 moves from a retreat start position C to the retreat position A via positions E and F after the abnormality signal is received by the NC unit 17. Then, after the exchange of tools has been completed, the tool 1 returns from the position A to the machining resumption position D via the positions F and E according to the return transfer steps in Table 1. FIG. 5, shows the retreat and return paths in the internal diameter mode.

As seen above, different predetermined retreat and return paths are provided for each mode to avoid interference between the cutting tool and workpiece.

Referring to FIG. 6, an NC machine tool 10 includes a chuck 11, a transfer table 13 which moves back and forth in the Z axis direction along a guide 12 and a tool table 14 which moves back and forth in the X-axis direction across the transfer table 13 and on which a tool 1 is provided.

An automatic tool exchange unit 16 is shown for automatically exchanging a damaged or abnormal tool 1, upon reaching the retreat positon A, with a new tool prepared elsewhere and stored in a tool magazine (not shown). An NC control unit 17 is for supplying predetermined operation command signals to the NC machine tool 10 and the automatic tool exchange unit 16 in accordance with programmed information inputted thereto. A tool abnormality detection unit 18 is for detecting abnormality of cutting tools during machining operation from, for example, a change of the main spindle motor current or the vibration in the machine tool.

Figure 3:
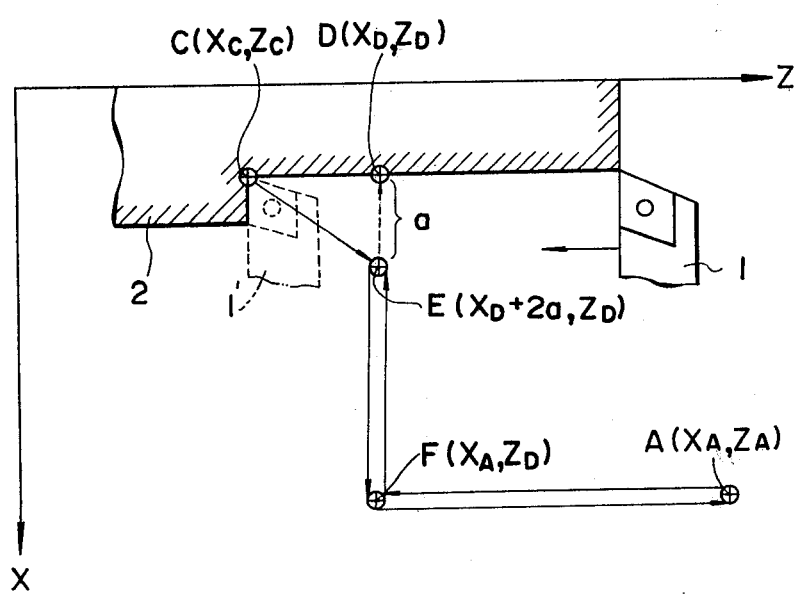
FIG. 3 shows retreat and return paths to be taken by the cutting tool when an abnormality occurs in the cutting tool during an external diameter machining operation.

Referring to FIG. 7, in the external diameter machining of a workpiece 2 by the tool 1, an external diameter machining program on NC tape is fed to the NC unit 17, which in turn outputs processed signals to a tool table driving motor 22 (hereafter called X-axis motor) and a transfer table driving motor 23 (hereafter called Z-axis motor or feed motor) via a change-over switch 20 and a pulse distributor 21 so as to transfer the tool 1 from the origin $P(X_P, Z_P)$ (FIG. 2) in accordance with a predetermined external diameter mode. When a tool abnormality occurs at a positon C (FIGS. 2 and 3) during the machining, the tool abnormality detection unit 18 detects the abnormality and outputs an abnormality signal $R_1$ to a control section 19 as well as the change-over switch 20. Upon receiving the abnormality signal $R_1$, the change-over switch 20 changes it position from NORMAL, by which the control section 19 is connected to the pulse distributor 21, to ABNORMAL, by which a sequence controller 24 is connected to the pulse distributor 21. In the meantime, upon receiving the abnormality signal $R_1$, the control section 19 stops outputting. At this time, a current position register 26 of a memory section 25 stores a current tool position, i.e., coordinates of an abnormality occurence position, and an NC command position register 27 stores a machining completion position B $(X_B, Z_B)$, derived from the normal machining program. The memory section 25 also includes a tool retreat position register 28 for storing coordinates $(X_A, Z_A)$ of the tool retreat position A, where an abnormal or damaged tool is exchanged, an X-axis minimum position register 29 for storing an X-axis minimum position a and a clearance parameter register 30 for storing clearance parameter l which is determined by the shape of the workpiece 2. The data stored in these registers are fed to an arithmetic circuit 31. The arithmetic circuit 31 selects either the external diameter mode, the edge face mode or the internal diameter mode according to a mode signal $R_2$ and then calculates the positions E and D on the retreat and return paths based on the data from these registers upon receiving a calculation start signal $R_3$. The values thus calculated are fed sequentially to a sequence controller 24. The sequence controller 24 outputs signals corresponding to its input signals to feed into the change-over switch 20 and the pulse distributor 21. The pulse distributor 21 feeds pulse signals into servo motors 22 and 23 for driving the tool table 14 and the transfer table 13, respectively so as to quickly move the tool 1 from the abnormality occurrence position C to the position E, then to the position F and further to the retreat position A, where the tool 1 is replaced by a new one. Thereafter, the newly installed tool 1 is moved into the positon F and then into the position E in the quick transfer manner, "quick". From the position E, the tool 1 is moved into the machining resumption position D while being operated in a machining manner. The machining resumption position D is deflected from the abnormality occurrence position C by an overlapped distance from C to D as shown in FIG. 3.

When the cutting tool has arrived at the machining resumption position D, the tool 1 moves to the abnormality occurrence position or retreat start position C in a machining mode by the instruction from the sequence controller 24. Then, the sequence controller 24 supplies an exchange completion signal $R_7$ to the control section 19 and transfers the change-over switch 20 into NORMAL position. Thus, the external diameter machining of the workpiece 2 resumes under command of the normal machining program. Since the machining resumption position D is located toward the machining start position from the abnormality occurrence position C by the overlapped distance, machining is performed twice over the abnormality occurrence area so as to remove any defect created by the tool 1 when the abnormality occurred.

Although the description has been made for the case of the external diameter machining, the method for deciding tool retreat and return paths according to this invention can also be applied to the cases of edge face machining and internal diameter machining.

Figure 8:
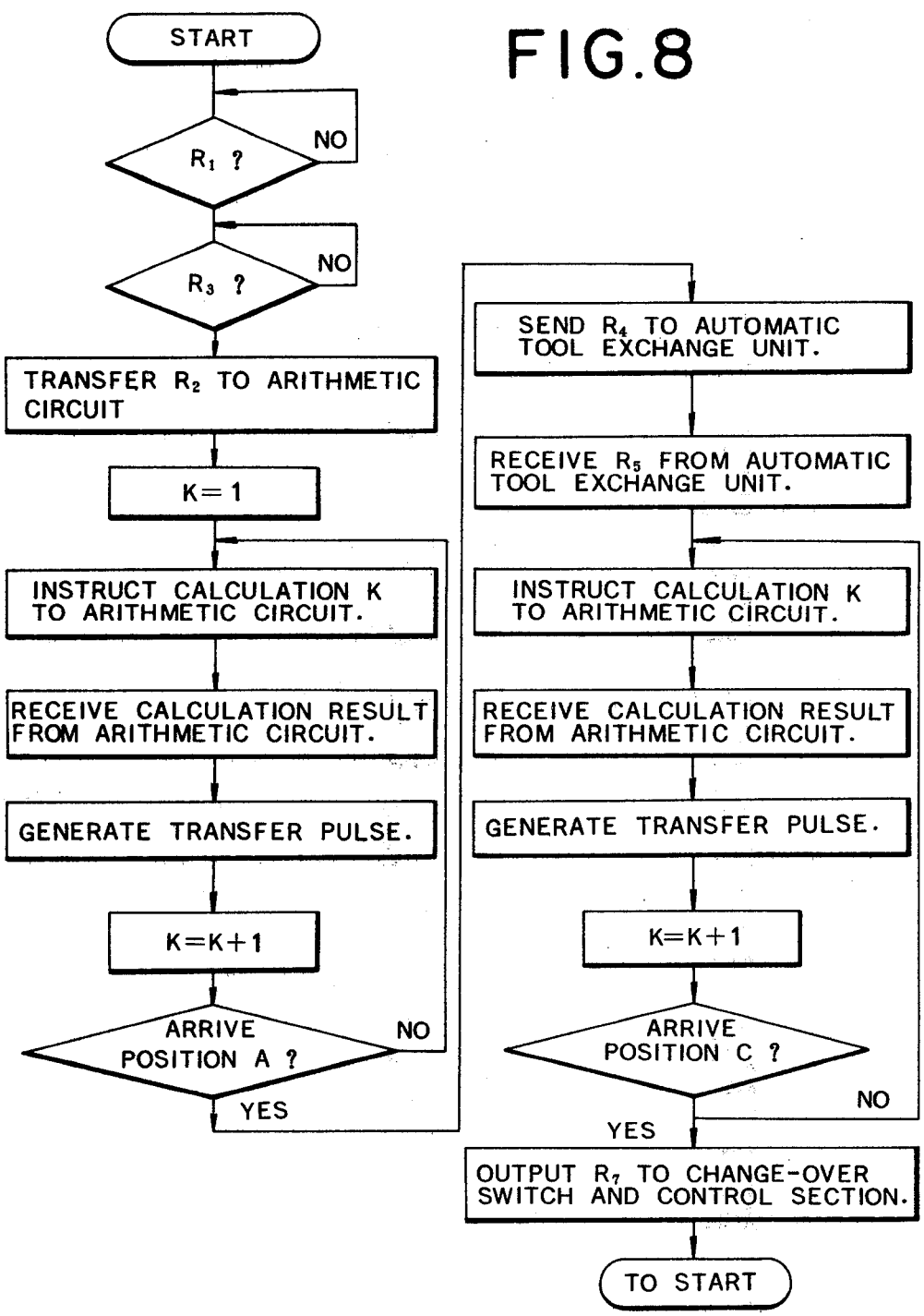
FIG. 8 is a flowchart showing the steps taken in an example of a sequence contoller, as disclosed herein.

Referring to FIG. 8, in the sequence controller 24, if the abnormality signal $R_1$ is received, the program sequence step is advanced to the next test and then if the calculation start signal $R_3$ is received, the program sequence step is again advanced. Then, the mode signal $R_2$ is transferred to the arithmetic circuit 31. The next step comprises instruction calculating by the arithmetic circuit 31, receiving calculation result therefrom and generating tool transfer pulses. The above step is repeatedly performed to transfer the tool to the position E. In transferring to the positions F and A, the same processes are conducted. When the tool has reached the retreat position A, the tool exchange signal $R_4$ is sent to the tool exchange unit 16 and after completion of exchanging tools, tool exchange completion signal $R_5$ is received. The next four steps for transferring the exchanged tool 1 to the positions F, E, D and C comprise the same processes as conducted in transferring to the position E described above. When the tool 1 arrives the position C, the exchange completion signal is sent both to the control section 19 and the change-over switch 20.

Figure 9A:
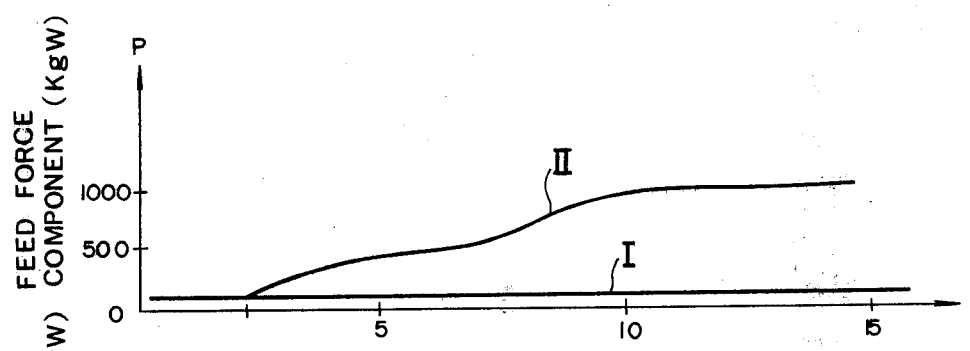
FIG. 9(a) and (b) are graphical representations showing the tool table feed force component with respect to time, and a spindle motor force component of the NC machine tool with respect to time, respectively.
Figure 9B:
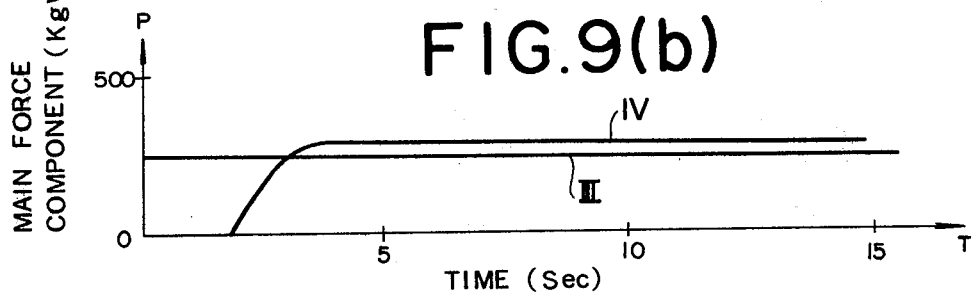

Referring to FIGS. 9(a) and (b), straight lines I and III show, respectively, the feed force component and the main force component in a normal machining condition. Curves II and IV show these components in an abnormal machining condition, respectively. The abnormal machining condition means that the tool 1 is being continuously damaged during machining. FIG. 9(a) shows that the feed force component greatly increases in the abnormal condition. However in FIG. 9(b), it is shown that the main force component does not change greatly in the abnormal condition.

Figure 10:
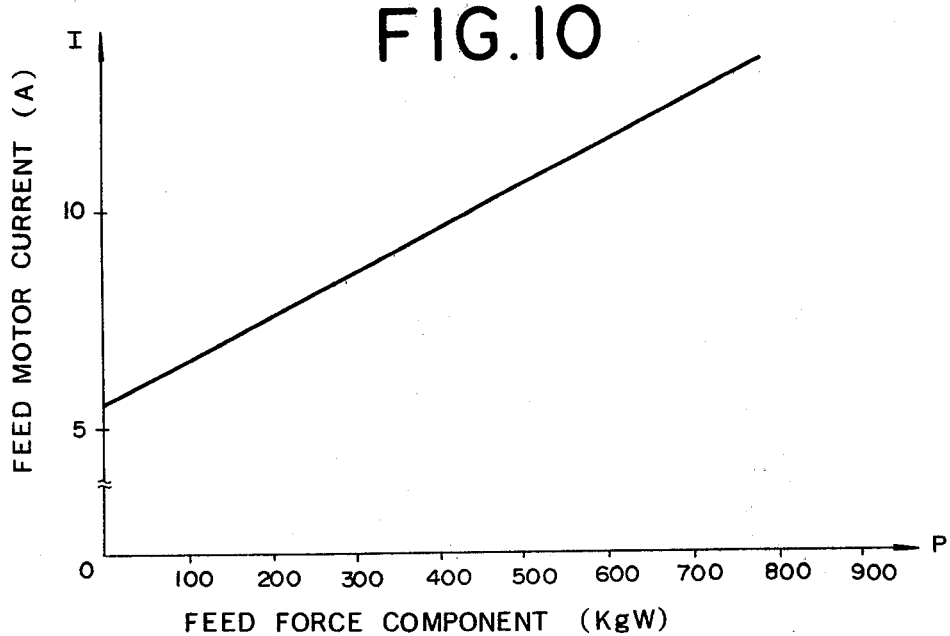
FIG. 10 is a graphical representation showing the relationship between a feed motor current and a feed force component.

Referring to FIG. 10, it is shown that a feed motor current I is proportional to the feed force component. Therefore, from FIG. 9(a) and FIG. 10, a relation is established that tool damage (abnormality) leads to a feed force component increase, which leads to increase in the feed motor current I.

Figure 11:
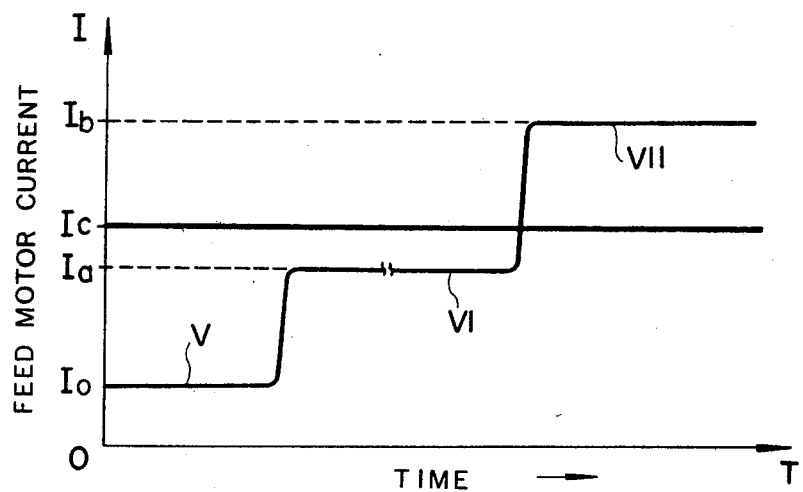
FIG. 11 is a graphical representation showing a transition of the feed motor current with respect to time, from noncontact of the cutting tool with the workpiece through normal machining to an abnormality of the cutting tool.

Referring to FIG. 11, a straight line V shows a feed motor current $I_0$ is a "no-load" condition prior to machining, that is, in transferring tool 1 without machining. The feed motor current $I_0$ becomes $I_a$, represented by a straight line VI, when a machining operation reaches the normal machining condition. When an abnormality such as tool damage and abnormal abrasion on the work occurs during machining, the current $I_0$ is further increased, for example to $I_b$ which is represented by a straight line VII. The current $I_b$ is from dozens of percent to several times larger than the current $I_a$ depending on cause and degree of the abnormality. Therefore, by setting a value $I_c$ which is larger than the current $I_a$ of the normal machining by a predetermined value as a threshold level and, by judging that the tool abnormality had occurred when the feed motor current I exceeds the threshold level $I_c$, the tool abnormality can be detected.

Figure 12:
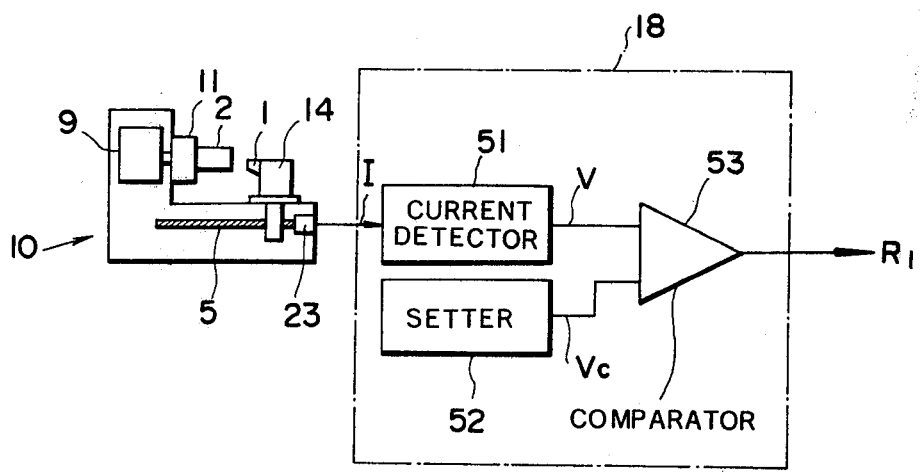
FIG. 12 is a diagram showing an example of a cutting tool abnormality detection unit connected to the NC machine tool.

Referring to FIG. 12, the main spindle motor 9 rotates the workpiece 2 which is held with the chuck 11 at a predetermined speed. The feed motor 23 drives a feed screw 5 to move the tool table 14, on which the tool 1 is provided. The tool abnormality detection unit 18 includes a current detector 51, a setter 52 and a comparator 53. The current detector 51 detects the feed motor current I and outputs a voltage signal V corresponding to the current I. The setter 52 is for setting the threshold current $I_c$ and outputs a set voltage signal $V_c$. The threshold current $I_c$ is larger than the feed motor current $I_a$ of the normal machining by a predetermined value (FIG. 11). The comparator 53 compares the input signal V with the set voltage signal $V_c$ and outputs the abnormality signal $R_1$ when the condition $V > V_c$ is established.

Figure 13:
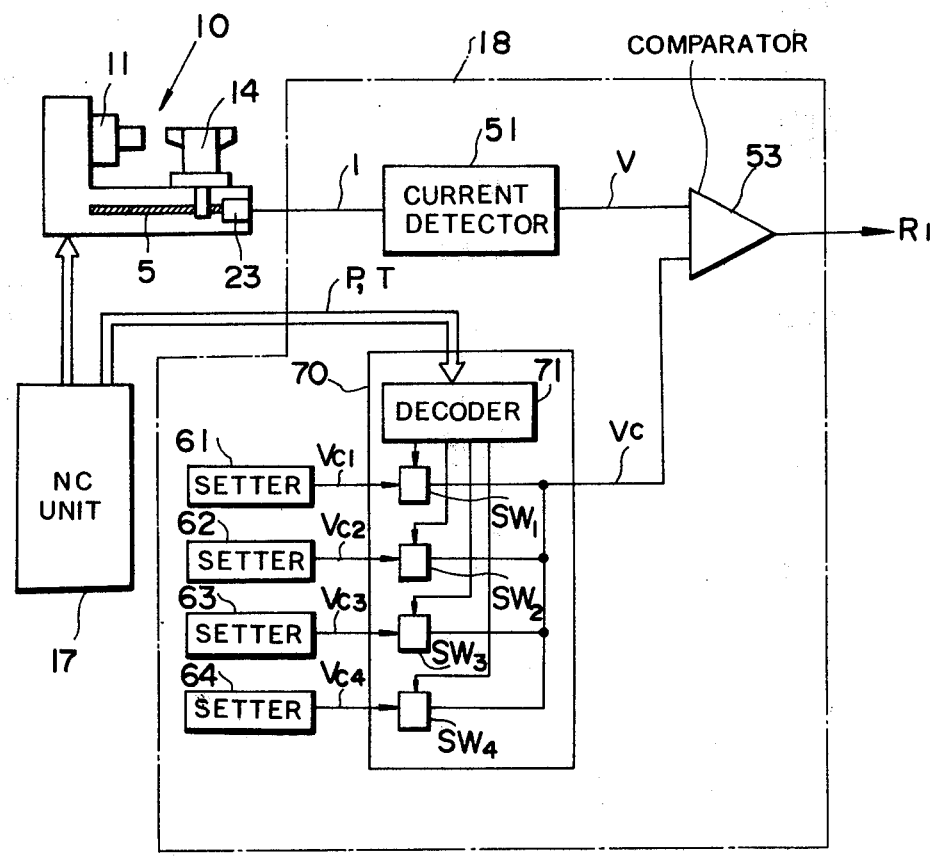
FIG. 13 is another example of the cutting tool abnormality detection unit connected to the NC machine tool.

FIG. 13 shows another example of the tool abnormality detection unit 18 in which a plurality of threshold levels are provided. Even during the normal machining, the feed force component of the tool table 14, that is, the feed motor current $I_a$ varies with portions of the work 2 being machined and types of tools being used. Therefore, a plurality of threshold levels are provided according to this variation. For example, four setters 61 through 64 are provided corresponding to four different threshold levels. These setters 61 through 64 output voltage signals $V_{c1}$ through $V_{c4}$ ($V_{c1} < V_{c2} < V_{c3} < V_{c4}$) corresponding to four different predetermined threshold currents and supply the output voltage signals to switching circuit $SW_1$ through $SW_4$ in a threshold level selection circuit 70. In the meantime, the NC unit 17 outputs control signals to the NC machine tool 10 to automatically control the NC machine 10 while supplying NC information such as a preliminary signal P code and a tool selection signal T code to a decoder 71 in the threshold level selection circuit 70. Upon receiving P code and T code, the decoder 71 converts these NC information into analog signals and supplies these analog signals to the switching circuits $SW_1$ and $SW_4$ to turn on one of the switching circuits in a predetermined manner. Through the switching circuit thus turned on, for example, the switching circuit SW2, an output signal $V_{c2}$ of the setter 62 is applied to the comparator 53. The comparator 51 compares the signal V from the current detector 51 with the set signal $V_{c2}$ and, if the condition $V > V_{c2}$ is established, outputs the abnormality signal $R_1$. As seen above, a threshold level to be used is selected out of a plurality of the threshold levels by the instruction of the NC information, and the abnormality signal $R_1$ is generated if the feed motor current I exceeds the threshold level thus selected.

Figure 14:
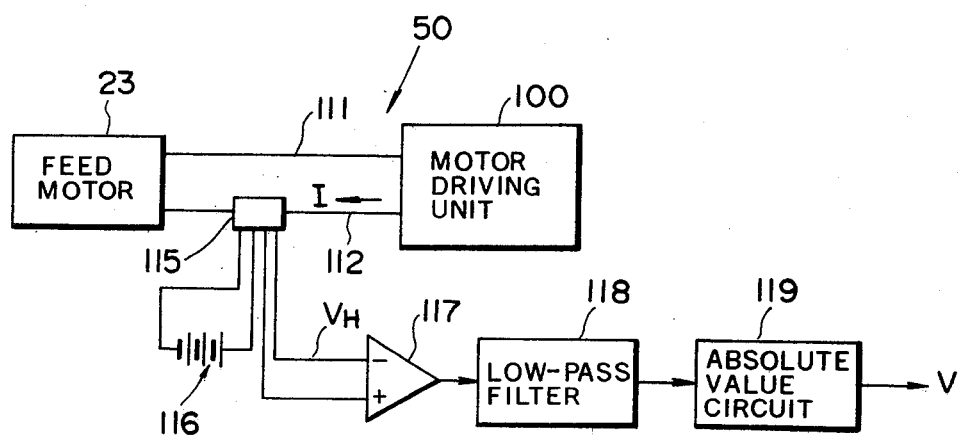
FIG. 14 is a block diagram showing an example of a feed motor current detector.

Referring to FIG. 14, a magnetic field generated by an armature current I (feed motor current) fed via cables 111 and 112 to the field-constant feed motor 23 is detected by a Hall element 115 so as to obtain a corresponding signal $V_H$. The signal $V_H$ is applied to an absolute value circuit 119 via a low-pass filter after being amplified by a differential amplifier 117, thus obtaining the voltage V corresponding to the feed motor current I in both normal and reverse rotations of the feed motor 23.

Figure 15:
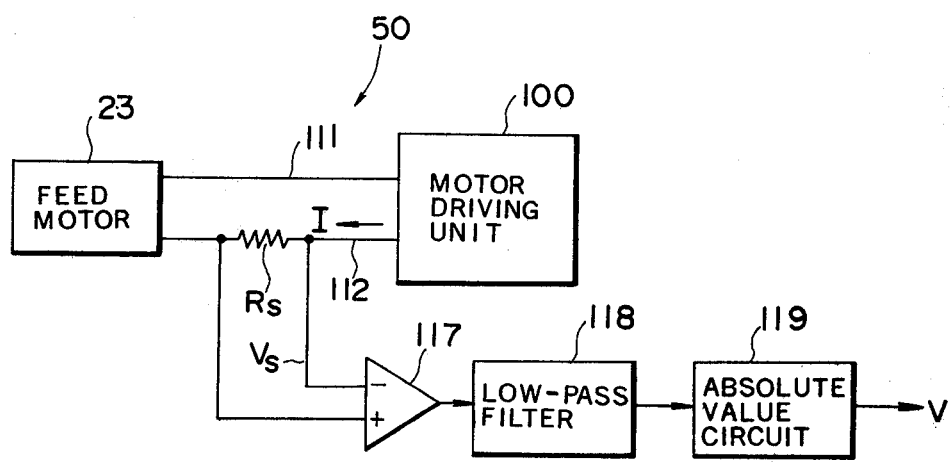
FIG. 15 is a block diagram showing another example of a feed motor current detector.

Referring to FIG. 15, a shunt resistor $R_s$ is provided at a cable 112 to obtain a voltage signal $V_s$. The signal $V_s$ is applied to the absolute value circuit 119 via the differential amplifier 117 and the low-pass filter 118 to obtain the voltage signal V corresponding to the the feed motor current I in both normal and reverse rotations of the feed motor 23.

Although, in the above embodiment, the tool is moved into the retreat position for exchange, it is possible for the tool to stay at the position E, and, if no abnormality is found in the tool, return directly to the position D.

We claim:

1. A method for automatically retreating and returning a cutting tool of a numerically controlled machine tool comprising:
   a step for retreating said cutting tool, when an abnormality arises in said cutting tool, into a first position, said retreat being in a direction and by a distance corresponding to a predetermined computational parameter selected in accordance with the type of machining operation to be performed on a workpiece; and
   a step for returning said cutting tool, after resolution of the cutting tool abnormality, via said first position into a second position determined by said parameter, said second position being such that machining of the workpiece is resumed to overlap a determined area machined prior to the occurrence of the cutting tool abnormality.

2. A method for automatically retreating and returning a cutting tool in a numerically controlled machine tool according to claim 1, wherein the cutting tool is retreated to said first position and returned via said first position into said second position along differing paths which are dependent upon the type of machining operation being performed.

3. A device for automatically retreating and returning a cutting tool in a numerically controlled machine tool comprising:
   switch means provided between a machining operations control section and a pulse distributor of a numerically controlled machine tool;
   memory means for storing data from which to determine tool retreat and return paths;
   tool abnormality detection means for detecting a cutting tool abnormality and outputting a tool abnormality signal to said switch means;
   an arithmetic circuit for calculating the tool retreat and return paths on the basis of the data stored in said memory means; and
   sequence control means provided between said arithmetic circuit and said switch means;
   said switch means switching in response to the tool abnormality signal so that the calculation results of said arithmetic circuit are applied to said pulse distributor via said sequence control means, thereby performing the retreat and return of the said cutting tool.

4. A device for automatically retreating and returning a cutting tool in a numerically controlled machine tool according to claim 3, wherein said switch means delivers to said pulse distributor the output of said machining operations control section, when in a normal machining operation, and the calculation results of said arithmetic circuit, via said sequence control means, during a retreat and return period subsequent to the cutting tool abnormality occurrence.

5. A device for automatically retreating and returning a cutting tool in a numerically controlled machine tool according to claim 3, wherein said memory means comprises registers for storing data indicating a cutting tool position when a cutting tool abnormality occurs, a cutting tool position where the normal machining operation is completed, a retreat position where the cutting tool is exchanged, a minimum allowable cutting tool position parameter, and a clearance parameter determined by the shape and size of the workpiece.

6. A device for automatically retreating and returning a cutting tool in a numerically controlled machine tool according to claim 3, wherein said cutting tool abnormality detection means detects a feed motor current and judges that a cutting tool abnormality occurs when the current thus detected exceeds a predetermined threshold value.

7. A device for automatically retreating and returning a cutting tool in a numerically controlled machine tool according to claim 5, wherein a plurality of threshold values are predetermined and cutting tool feed motor current is sensed and compared with one of said plurality of predetermined threshold values in accordance with an identifiable machining condition and type of cutting tool being used so as to judge a cutting tool abnormality occurrence.

8. In a numerically controlled machine tool comprising:
   means for holding a workpiece in a rigid, translatable, or rotatable manner,
   means for translating or rotating said workpiece along with its holding means;
   a cutting tool;
   means for holding said cutting tool, said tool holding means being automatically translatable in at least two dimensions so as to perform machining operations on said workpiece;
   means for driving said tool holding means in said at least two dimensions; and
   numerical control means for interpreting preprogrammed machining instructions and providing sequential commands to said driving means to advance or retreat said cutting tool along a desired path in at least two dimensions;
   the improvement consisting of:
   cutting tool monitor means for continuously sensing status of said cutting tool, and for detecting and communicating a signal whenever the sensed status indicates an abnormality in the said cutting tool;
   switching means, operating on receipt of the abnormality indication signal from said cutting tool monitoring means, for interrupting the normal sequence of interpretation of the preprogrammed machining instructions and the normal provision of sequential commands to said tool holder driving means, and for then enabling automatic retreat of said abnormal cutting tool, via a computed translational path, avoiding contact with the workpiece, to a position whereat the abnormal cutting tool is replaced, and for then returning the new cutting tool, via a computed translational path, to a return position whereat machining is resumed, said return position being such that a portion of the preprogrammed machining is repeated, and, upon reaching the cutting tool position at which the abnormality indication signal occurred, for then restoring the normal sequence of machining under the same numerical control means;

memory means, for retaining (a) information of the position of said cutting tool at which said abnormality indication arose, (b) the expected a position of said cutting tool upon completion of the normal machining operation, (c) the position of said cutting tool whereat a cutting tool exchange is to be performed, (d) a parameter describing the type of machining being performed, and (e) a clearance parameter dependent on the size and shape of said workpiece;

an arithmetic unit, preprogrammed for computing the translational retreat and return paths, based upon the information retained in said memory means, such that the cutting tool, in following said paths, will avoid contact with the workpiece; and a sequence control means, for converting said path information to sequential driving commands which are provided to said driving means to perform the determined translations until said switching means restores operation to said numerical control means.

9. A method for automatically retreating and returning a cutting tool of a numerically controlled machine tool, including within the normal control means of said numerically controlled machine tool information identifying the mode of machining operation being performed, together with means to recognize and communicate said mode identification information; comprising:

a first step, wherein the occurrence of an abnormality in said cutting tool is detected, by abnormality detection means, and a signal is communicated to the normal control means so as to interrupt operation of the normal control means of said numerically controlled machine tool;

a second step, wherein a cutting tool retreat path is determined from information identifying the type of machining operation being performed and cutting tool positional information, together with an input parameter characterizing the size and shape of a workpiece, such that said path is in a direction and for a distance so as to avoid contact of said cutting tool and said workpiece during translation along said return path, said path terminating in a retreat position;

a third step, wherein the determined retreat path information is transformed into sequential commands for execution by said numerically controlled machine tool causing the rapid translation of the cutting tool to said retrect position;

a fourth step, wherein a cutting tool return path is determined from the information utilized in the second step, above, such that said return path results in the return of said cutting tool to machining contact with said workpiece at a position preceding, in the normal machining sequence, that at which the abnormality in said cutting tool was detected;

a fifth step, wherein the determined returned path information is transformed into sequential commands for execution for said numerically controlled machine tool causing the rapid translation of said cutting tool to said return position;

a sixth step, wherein a retained segment of the normal machining sequence of commands are provided to the numerically controlled machine tool to cause the cutting tool to remachine said workpiece from said return position to the position at which the abnormality in said cutting tool was detected; and a seventh step, wherein the interruption of the normal control means of said numerically controlled machine tool is terminated, and said normal control means resumes command of the machining operation.

10. In an apparatus in which a cutting tool is moved along a preprogrammed path to accomplish the cutting of a workpiece, the improvement comprising:

abnormality detection means for detecting an abnormality of said cutting tool during said cutting operation, retreat control means, operative upon detection of said abnormality by said detection means, for directing the retreat of said cutting tool away from said workpiece along a path computed by taking into account the preprogrammed cutting path and the shape of the said workpiece, said retreat control means moving said cutting tool through a first retreat position clear of said workpiece to a second position at which said cutting tool may be replaced, and return control means for directing the return of the replaced cutting tool along a path which passes through said first retreat position to a point along said preprogrammed cutting path prior to the point at which said abnormality was detected, movement of said cutting tool thereafter following said preprogrammed cutting path so that the portion of the cutting operation accomplished immediately before abnormality detection is repeated, and the remainder of the cutting operation is completed along said preprogrammed path.

11. An apparatus according to claim 10 wherein said cutting tool is driven by a feed motor, and said detection means detects said abnormality by monitoring the current to said feed motor.

* * * * *